United States Patent
Manesis

[19]

[11] Patent Number: 6,164,495

[45] Date of Patent: Dec. 26, 2000

[54] METERED DISPENSING DEVICE

[76] Inventor: Nick J. Manesis, 7255 Girard Ave., Ste. 27W, La Jolla, Calif. 92037

[21] Appl. No.: 09/432,191

[22] Filed: Nov. 2, 1999

[51] Int. Cl.$^7$ ........................................................ B67D 5/56
[52] U.S. Cl. ................... 222/129; 222/144.5; 222/145.1; 222/145.5
[58] Field of Search ............................... 222/129, 144.5, 222/145.1, 145.5; 206/219, 222; 215/DIG. 8

[56] References Cited

U.S. PATENT DOCUMENTS

| | | | |
|---|---|---|---|
| 3,768,697 | 10/1973 | Lerner | 222/145.5 |
| 3,802,604 | 4/1974 | Morane et al. | 222/145.1 |
| 4,122,943 | 10/1978 | Silver et al. | 206/221 |
| 4,465,183 | 8/1984 | Saito et al. | 206/222 |
| 4,682,689 | 7/1987 | Pereira et al. | 206/222 |
| 4,693,366 | 9/1987 | Goncalves | 206/222 |
| 4,757,916 | 7/1988 | Goncalves | 222/145.5 |
| 4,982,875 | 1/1991 | Pozzi et al. | 222/83 |
| 5,170,888 | 12/1992 | Goncalves | 206/219 |
| 5,353,928 | 10/1994 | Schumacher | 206/222 |
| 5,388,690 | 2/1995 | Mutterle et al. | 206/222 |
| 5,622,287 | 4/1997 | Glynn | 222/321.8 |
| 5,782,345 | 7/1998 | Guasch et al. | 206/222 |
| 5,967,377 | 10/1999 | Glynn | 222/158 |

*Primary Examiner*—Kevin Shaver
*Assistant Examiner*—Thach H Bui
*Attorney, Agent, or Firm*—Frank G. Morkunas

[57] ABSTRACT

A dispensing device having a first member connectable to a container which has a passage. A second member is movably connectable to the first member. A registration mechanism reflects a first position and a second position as the members are moved relative to each other. The first member has a mixing chamber, with one or more capillaries, and an opening; each in communication with the passage of the container. The second member has a dispensing chamber, to hold Fluid-1 for dispensement, and an outlet. In the first position, the outlet is in discharge communication with the opening permitting discharge from the outlet of Fluid-2 in the container. During relative movement when the device is between the first and second positions, the outlet is sealed from the opening and the capillaries, and the dispensing chamber passes over the mixing chamber depositing Fluid-1 into the mixing chamber. In the second position the mixing chamber is in discharge communication with the outlet permitting Fluid-2 from the container to pass through the mixing chamber, mix with Fluid-2, and exit the outlet co-mixed.

17 Claims, 2 Drawing Sheets

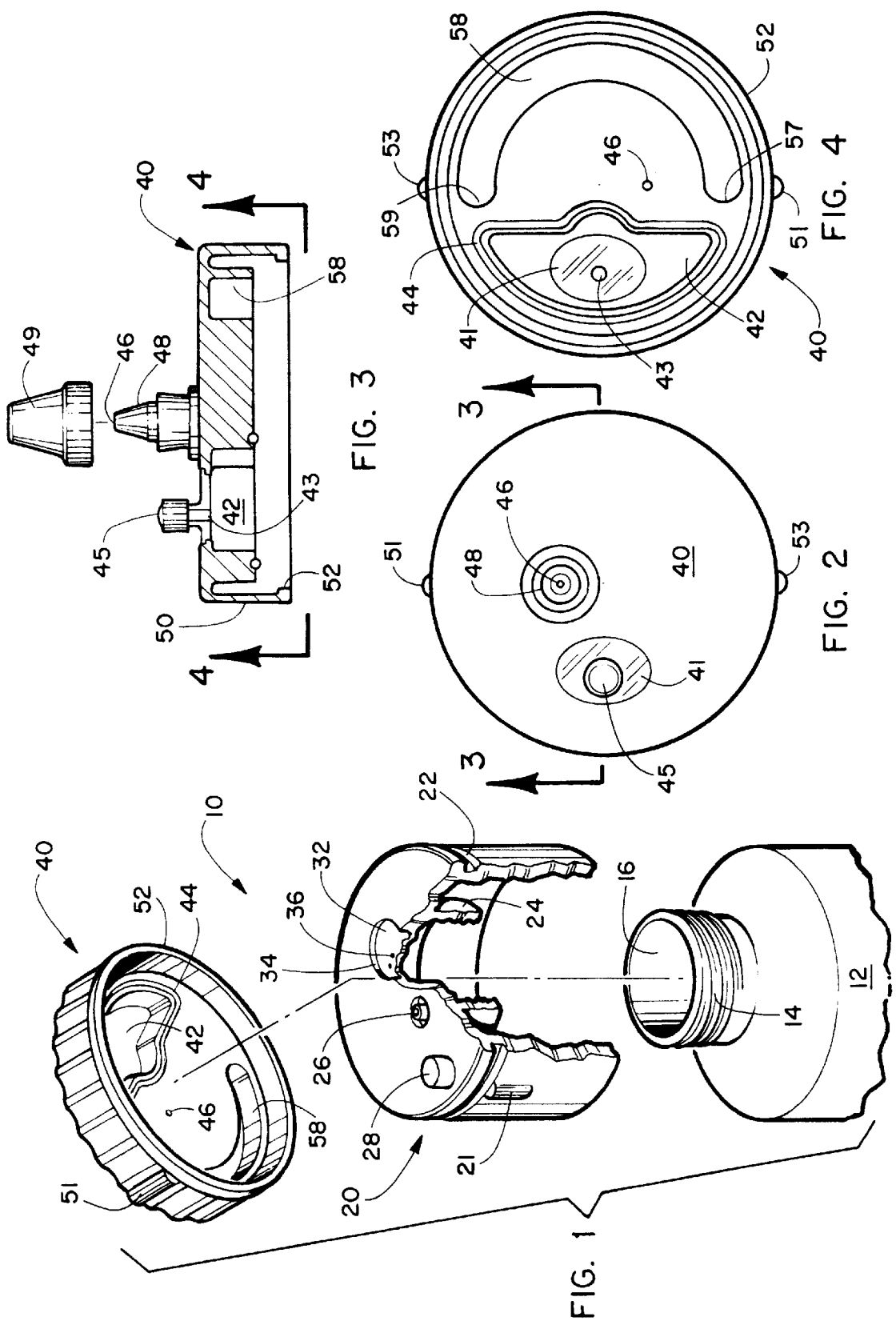

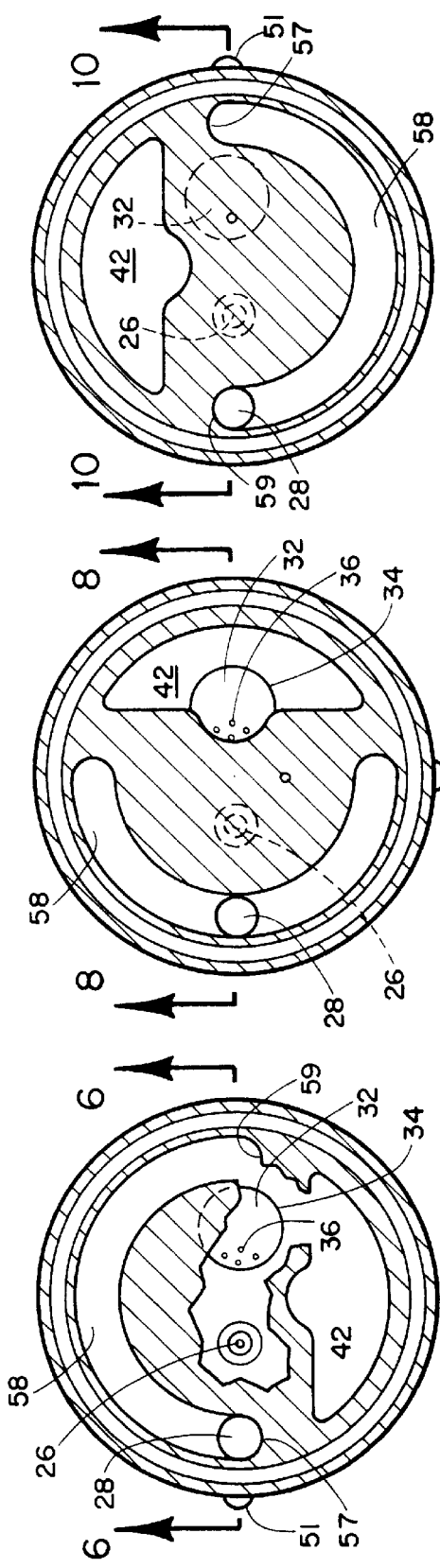

METERED DISPENSING DEVICE

CROSS REFERENCES TO RELATED APPLICATIONS

Not applicable.

STATEMENT REGARDING FEDERALLY-SPONSORED RESEARCH OR DEVELOPMENT

Not applicable.

BACKGROUND OF THE INVENTION

This present invention relates to an improvement in devices for dispensing fluids, and more particularly to devices containing one fluid-substance fitted onto containers housing another fluid-substance and to mix these fluid-substances while dispensing them co-mixed for ultimate use. For discussion purposes only, the focus will be on eye-care solutions such as disinfecting solutions, cleaning solutions, rinsing solutions, storing solutions, protein-removal solutions and tablets, and the like. It must be understood, however, that this device may be fitted onto any external container and thereby mix one fluid-substance contained within the device with another one or more fluid-substances housed within the external container for final use.

Many people wear corrective lens in the form of glasses or contact lenses. For contact lenses there are daily wear (insert, wear, remove, disinfect, and clean daily), extended wear (insert and wear for several days at a time before removing, disinfecting, and cleaning), and disposable (insert and wear for a certain length of time, remove, and discard). In non-disposable form, contact lenses require routine maintenance which includes disinfecting (to kill potential sight-threatening microorganisms) and cleaning (to remove biomolecules and debris deposited on the lens).

Routine maintenance requires numerous solutions and in many cases, mixing of several solutions or tablets in pre-determined ratios. This is particularly true for proper removal of protein deposits on the lens surfaces. Either an enzymatic tablet or an enzymatic solution, mixed with another eye-care solution (usually a disinfectant) in proper approximate ratios is required. The process can be cumbersome, trying, difficult, and subject the user to misuse conditions. To date, no device or method has been found to make this task easier and simpler. Some mixing bottles/containers have been devised for various purposes, especially pharmaceutical purposes. Some can be found in U.S. Pat. No. 4,757,916 issued to Goncalves on Jul. 19, 1988; U.S. Pat. No. 4,982,875 issued to Pozzi, et. al., on Jan. 8, 1991; U.S. Pat. No. 5,388,690 issued to Mutterle, et. al., on Feb. 14, 1995; and U.S. Pat. No. 5,782,345 issued to Guasch, et. al., on Jul. 21, 1998. Each of these prior art devices, though well-suited for the intended purpose, are either complicated to use; complicated in construction having piston, droppers, perforators, and/or collars; costly to manufacture; and require considerable effort and manipulation to properly mix two or more fluid products or substances. All prior-art devices involve mixing of all components/fluids at one time. Moreover, none is a simply constructed, easy-to-use, easy-to-mix, readily adaptable device, nor capable of multiple-mixing uses, as is the present invention.

Accordingly, several objects and advantages of the present invention are to:

a. provide a simple construction for use with existing, or constructable, containers which mixes two fluid substances into one usable solution immediately prior to use;

b. provide a simple-to-use mixing capability of desired fluids in desired proportions immediately prior to each use;

c. create a low-cost, simple-to-manufacture, and easy-to-use mixing device;

d. permit the user the option to by-pass mixing of the two fluid-substances to thereby dispense an unmixed fluid-substance;

e. limit the number of steps required to use the device and to mix the two fluid-substances;

f. eliminate the need for special equipment or special manipulations for use; and g. provide for a minimum range-of-motion necessary to use the device.

The foregoing has outlined some of the more pertinent objects of the present invention. These objects should be construed to be merely illustrative of some of the more prominent features and applications of the intended invention. Many other beneficial results can be attained by applying the disclosed invention in a different manner or by modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

BRIEF SUMMARY OF THE INVENTION

The above-noted problems, among others, are overcome by the present invention. Briefly stated, the present invention contemplates a dispensing device attachable to a container having a passage. The dispensing device has a first member connectable to the container and a second member rotatably connectable to the first member with registration to reflect a first position and a second position. The first member has a mixing chamber with one or more capillaries therein and an opening, each in communication with the passage of the container. The second member has a dispensing chamber for holding one fluid or liquid substance (fluid-1) and an outlet, which when the device is in the first position, the outlet is in dispensing communication with the opening of the first member such that another fluid or liquid substance in the container (fluid-2) is dischargeable from the outlet, and when rotated to the second position the dispensing chamber passes over the mixing chamber depositing fluid-1 into the mixing chamber such that, when stopped in the second position, the mixing chamber is in communication with the outlet such that as fluid-2 in the container is discharged therefrom it (fluid-2) passes through the mixing chamber and discharges from the outlet fluid-2 combined with fluid-1. During rotation when the device is in between the first and the second position, the outlet is sealed from the opening and the capillaries.

The foregoing has outlined the more pertinent and important features of the present invention in order that the detailed description of the invention that follows may be better understood so the present contributions to the art may be more fully appreciated. Additional features of the present invention will be described hereinafter which form the subject of the claims. It should be appreciated by those skilled in the art that the conception and the disclosed specific embodiment may be readily utilized as a basis for modifying or designing other structures and methods for carrying out the same purposes of the present invention. It also should be realized by those skilled in the art that such equivalent constructions and methods do not depart from the spirit and scope of the inventions as set forth in the appended claims.

BRIEF DESCRIPTION OF THE DRAWINGS

For a fuller understanding of the nature and objects of the invention, reference should be had to the following detailed description taken in conjunction with the accompanying drawings in which:

FIG. 1 is an exploded perspective view of the dispensing device attachable to an external container.

FIG. 2 is a top plan view of the dispensing device.

FIG. 3 is a cross-sectional view taken on line 3—3 of FIG. 2 of the top member of the dispensing device.

FIG. 4 is a bottom plan view taken on line 4—4 of FIG. 3 of the top member of the dispensing device.

FIG. 5 is cross-sectional plan view of the top member taken on line 5—5 of FIG. 6 with a portion cut-away exposing the bottom member.

FIG. 6 is a cross-section view of the dispensing device as taken on line 6—6 of FIG. 5.

FIG. 7 is cross-sectional plan view of the top member taken on line 7—7 of FIG. 8 with a portion cut-away exposing the bottom member.

FIG. 8 is a cross-section view of the dispensing device as taken on line 8—8 of FIG. 7.

FIG. 9 is cross-sectional plan view of the top member taken on line 9—9 of FIG. 10 with a portion cut-away exposing the bottom member.

FIG. 10 is a cross-section view of the dispensing device as taken on line 10—10 of FIG. 9.

DETAILED DESCRIPTION OF THE INVENTION

Referring now to the drawings in detail and in particular to FIG. 1, reference character 10 generally designates a dispensing device constructed in accordance with a preferred embodiment of the present invention. For the purpose of this disclosure and the claims which follow, the terms 'fluid' and 'liquid' refer generically to a relatively free-flowing substance be it water-like product or substance or a fine powder or powder-like product or substance which, if combined, form solutions. In this regard, the present invention may be adapted to attach to any existing external container 12. Such containers should generally have a passage or mouth 16 from which fluid(s) from within may flow out. The external container 12 may, but need not, have a collar or spout 14. It is preferable that the container 12 have a mouth capable of accepting the present invention. As such, it is preferred that the mouth 16 or spout 14 of the container have threading, channels, ridges, and the like to receive and retain the present invention.

Turning to the details of the present invention and to FIGS. 1–4 for reference, the preferred embodiment comprises a first member 20 and a second member 40. The first member 20 has an attachment member 24 adapted to attach to the mouth 16 or collar 14 of the external container 12. In this regard, the attachment member 24 may have threading corresponding to the threading on the external container 12, may have ribs corresponding to the channels of the external container, may have channels corresponding to the ridges of the external container, may be comprised of suitable detents, bayonet-type fittings, or be a friction-fit connection. The present invention may also be molded and directly fused onto an external container 12 during the manufacturing process of the container itself. Any conventional mechanism or method of attaching will suffice. What is important here is the device 10 and its structure and dispensing functions.

An index 21 is illustrated on the side of the firs member 20. The purpose of this index 21 will be explained later. On the first member 20 there is an opening 26 which is a passageway through the first member 20. The opening 26 is positioned such that it lies on the inside perimeter of the attachment member 24 and, when attached to the external container 12, is in communication with the fluid housed within the external container 12. A depression on top of the first member 20 defines a mixing chamber 32. Within this mixing chamber 32 is/are one or more tiny capillary-like aperture(s) 36. The capillaries, as with the opening 26, also are positioned such that they lie on the inside perimeter of the attachment member 24 and, as structured, are in limited (or one-way) communication with the fluid housed within the external container 12. The attachment member 24 also may be, but need not be, structured such that its perimeter completely encompasses the mixing chamber 32 above.

As illustrated in this embodiment, adjacent to the perimeter of the mixing chamber 32 is a seal 34. The function of the seal 34 is to keep in fluids deposited within the mixing chamber 32 and to prevent unwanted fluids from being deposited into and contaminating the mixing chamber 32 and/or from contaminating fluids already within the mixing chamber 32. It must be understood that this sealing member may or may not be employed on the present invention. Configuring the present invention with this sealing member will depend on the intended use and desired result.

Also on the top surface of the first member 20 is a protuberance 28 which mates with the channel 58 located on the underside of the second member 40. Another channel 22 is defined on the outer surface of the side wall of the first member 20. The structure and functions of each of these (protuberance 28/channel 58 and channel 22) will be explained later.

A depression on the underside of the second member 40 defines a dispensing chamber 42. A sealing member 44 adjacent to the perimeter of the dispensing chamber 42 serves a two-fold purpose. First, it prevents fluid within the dispensing chamber 42 from escaping from the dispensing chamber 42 and, second, it prevents unwanted fluids from entering and contaminating fluids inside the dispensing chamber 42. This sealing member 44 may be of any material or substance suited for the intended purpose, including, but not limited to, silicone, rubber, vinyl, polymer, or a cork-like material. It must be understood that this sealing member, similar to the previously described sealing member, may or may not be employed on the present invention. Configuring the present invention with this sealing member will depend on the intended use and desired result.

An outlet 46 provides clear outward passage of fluids from the inside of the second member 40. The outlet 46 may, but need not, have a cap device 49 attachable thereto and/or removable therefrom for the purpose of preventing spillage if not capped. An upstanding spout 48 or similar object may be crafted onto the top of the second member 40 to facilitate and direct the flow of fluids exiting the dispensing device 10. Channel 58, on the underside and inside the side walls of the second member 40, is adjacent to, and internal of, the outer perimeter of the second member 40. An inwardly extending lip or rib 52 is illustrated on the bottom of the side wall of the second member 40. As the second member 40 is attached to the first member 20, the channel 58 of the second member 40 is placed over and movably mates with the protuberance 28 of the first member 20. As the second member 40 is so placed, the lip 52 seats into the channel 22 on the side wall of the first member 20. As so seated, the second member 40 is rotatable about the first member 20. The rotation of the second member 40 is limited by the length of the channel 58 as the channel 58 moves or glides about the protuberance 28 until either end of the channel 58 strikes the protuberance 28 and halts the rotation. The respective end points 57, 59 define and register a first position (FIGS. 5, 6) and a second position (FIGS. 9, 10).

In addition, or in lieu of, the registration for the first position and the second position by way of the channel 58 and its mated stop 28, FIGS. 5–10 illustrate another registration mechanism embodying a primary register 51 on the side wall of the second member 40 and two secondary registers 21 and 23 on the side wall of the first member 20. These two secondary registers are to be aligned with the primary register 51. The first position is attained with one secondary register 21 aligned with the primary register 51 as illustrated in FIGS. 5 and 6; the second position is attained with the other secondary register 23 aligned with the primary register 51 as illustrated in FIGS. 9 and 10. Without the channel 58 and stop 28 described earlier, a user may manually set the dispensing device 10 for the first or the second position. In a device 10 fitted with the channel 58 and stop 28, a user need only rotate the second member 40 in either direction up to the stop point. At one end-point 57 of the channel 58, the device is in the first position and at the other end-point 59 of the channel 58, the device is in the second position.

The locations of the primary register and secondary registers may be inverted with the primary register 21 being on the side wall of the first member 20 and the two secondary registers 51, 53 being on the side walls of the second member 40. Reference is made to FIGS. 1, 2, and 4. For illustration purposes only the Figures represent these registration mechanisms in exaggerated form. In any event, these registration mechanisms and indexes may be any form of indicia on the respective members 20, 40; may be grooves, channels, nubs, or any combination thereof. What is important is that they are visible or tactile and are suited for alignment.

It also must be understood that the channel 58 and stop 28 which are illustrated to be on the second (or top) member 40 and the first (or bottom) member 20, respectively, and the lip 52 and channel 22 which also are illustrated to be on the second (or top) member 40 and the first (or bottom) member 20, respectively, may be cooperatively structured to be on the other such member 20, 40. The device 10 may be structured with the rotational capabilities for the second member to range between 10° and 350°; that is, with the end points 57, 59 of the channel 58, if drawn to the center of the second member, would form an angle of between 10° and 350°. The preferred angles best suited for this purpose, however, I have found to be approximately 90–180°.

The significance of the first position and the second position is important. In the first position, fluid-1 in the dispensing chamber 42 remains securingly retained within. Only fluid-2 from the external container 12 will pass through the mouth 16, pass through the first member 20 via the opening 26, pass through the second member 40 via the outlet 46, and completely out. Fluid-2 of the external container 12 does not mix with fluid-1 within the dispensing chamber 42 or with fluid-1 within the mixing chamber 32.

As the second member 40 is moved either from the first or the second position (FIGS. 5, 6, 9 and 10), this action causes the dispensing chamber 42 to move and pass over the mixing chamber 32. As this pass occurs, fluid-1 within the dispensing chamber 42 deposits into and fills the mixing chamber 32. When the rotation of the second member 40 comes to rest into the second position (FIGS. 9, 10), as a user dispenses with fluid-2 from the external container 12, it will first pass through the opening 16 and then will pass through the first member 20 via the capillaries 36 instead of the opening 26, followed by a pass through the second member 40 via the outlet 46, and completely out. In this execution, fluid-2 from the external container 12, as it passes through the mixing chamber 32, combines and mixes with fluid-1 now contained in the mixing chamber, and out providing the user with pre-mixed solution for immediate use.

Significant here is that the capillar(y)(ies) 36 is/are structured such that fluid-1 contained within the mixing chamber 32 is retained therein and cannot pass down through and into the external container 12 (held thereat by natural physico-chemical and mechanical forces). By way of example only, and not by way of limitation, the aperture(s) could range in diameter from approximately 0.005–0.100 inches. I have found that a diameter of 0.010–0.020 inches provides better retention for the device 10. Also significant to the present invention is that, while the second member 40 is being rotated and is between the first and the second position (FIGS. 7, 8), the opening 26 is sealed thereby. At this stage, there is no discharge communication between the outlet 46 and the opening 26 or, consequently, between the outlet 46 and the passage 16. This is the result of the bottom surface of the second member 40, which is relatively flat and abutting the upper surface of the first member 20, covering the opening 26 as the second member 40 is rotated. Simultaneously, the capillaries 36 within the mixing chamber 32 are sealed from, and not in discharge communication with, the outlet 46 of the second member 40 until the device 10 is in the second position. To better accomplish the above sealing function, a preferred embodiment has the center of the mixing chamber 32 in approximate linear alignment with the center of the opening 26 and the center of the attachment member 24 while the center of the outlet 46 is in approximate vertical alignment with the center of the opening 26 in the first position and in approximate vertical alignment with the center of the mixing chamber 32 in the second position.

As so structured, therefore, non-mixed fluid from the external container 12 may be discharged from the outlet 46 only* when the dispensing device is in the first position (FIGS. 5, 6). (NOTE: *non-mixed fluid also may be discharged in the second position, FIGS. 9 and 10, when the mixing chamber 32 is devoid of fluid-1). The route and passageway for this first position is from the mouth 16, through the opening 26, and through the outlet 46. Mixed solution (fluid-2 from the container 12 and fluid-1 from the mixing chamber 32) may be discharged from the outlet 46 only when the dispensing device is in the second position (FIGS. 9, 10). The route and passageway for this position is from the mouth 16, through the capillaries 36 within the mixing chamber 32, and through the outlet 46.

In situations where the dispensing chamber 42 is empty, and to prevent or minimize instances of non-mixed fluid, rather than a mixed solution, being discharged from the outlet 46 when the user positions the dispensing device 10 in the second position and intends to discharge mixed solution, I have fashioned a viewer or window 41 above and adjacent to the dispensing chamber 42. The viewer 41 is comprised of transparent or translucent material such that the volume of fluid-1 within the dispensing chamber 42 is discernible. A fill tube or conduit 43 above and adjacent to the dispensing chamber 42 permits a user to replenish the depleted fluid-1. A removable cap-like member 45 engages the fill tube to prevent fluid-1 from escaping.

It must be understood that either the view member 41 or the fill tube 43 or both may be structured on the second member 40 for the purpose of detecting the volume of fluid-1 within and/or replenishing fluid-1 as the need arises.

Different fluids are used for different purposes and generally require varying ratios for proper use. In order for proper mixing for particular use, the total volume of solution ultimately dispensed from the outlet 46 must be known. This total is referred to as "C". C being known for a use is dependent on the use and is, thereby, fixed for that particular use. Ratios between two fluid substances (fluid substance A and fluid substance B) also must be known. In this regard, A is fluid-2 contained within an external container 12. B is fluid-1 contained with the dispensing chamber 42. A and B are to be co-dispensed in proper proportion in the mixing chamber 32 for ultimate discharge through the outlet 46 into a cup or cups (bearing a total volume of C) for use. By way of example only, and not by way of limitation, in the case of eye care using contact lenses and having one cup for both lenses. The combined volume of the cup is C, a pre-determined known. The capacity of the mixing chamber 32 is referred to as "N". The required ratio between A and B is also a pre-determined known for a particular purpose. The quantity of A needed for this pre-determined is referred to as QA; the quantity of B needed for this predetermined ratio is referred to as QB. C, therefore, equals QA+QB and N is dependent on QB.

Once the purpose of the solution, the volume of C, and the ratios for A and B are established, dispensing devices may be produced for the particular purpose following these principles:

$C$ is constant; $C=QA+QB$; and $N=QB$;

In this manner N drives the volume-size of the mixing chamber 32 when C is a pre-determined quantity/volume.

The present disclosure includes that contained in the present claims as well as that of the foregoing description. Although this invention has been described in its preferred forms with a certain degree of particularity, it is understood that the present disclosure of the preferred forms has been made only by way of example and numerous changes in the details of construction and combination and arrangement of parts may be resorted to without departing from the spirit and scope of the invention. Accordingly, the scope of the invention should be determined not by the embodiments illustrated, but by the appended claims and their legal equivalents.

The invention claimed is:

1. A dispensing device attachable to a container having a passage, said device comprising:
   a. a first member connectable to the container, said first member having an opening in communication with the passage of the container and further having a mixing chamber with one or more capillaries therein in communication with the passage of the container;
   b. a second member movably attachable to said first member, said second member having an outlet and further having a dispensing chamber for holding a liquid substance, which when said second member is in one position, said outlet is in dispensing communication with said opening of said first member such that a fluid substance in the container is dischargeable from said outlet, and when said second member is moved to a second position said dispensing chamber passes over said mixing chamber depositing the liquid substance into said mixing chamber such that, when in said second position, said mixing chamber is in communication with said outlet such that as the fluid substance is discharged from the container it passes through said mixing chamber and discharges from said outlet the fluid substance combined with the liquid substance.

2. The device as defined in claim 1 further comprising a mixing containment means for preventing the liquid substance from migrating from said mixing chamber.

3. The device as defined in claim 2 wherein said mixing containment means comprises a seal.

4. The device as defined in claim 1 further comprising a dispensing containment means for preventing the liquid substance from migrating from said dispensing chamber.

5. The device as defined in claim 4 wherein said dispensing containment means comprises a seal.

6. The device as defined in claim 1 further comprising a primary index on said first member and at least two secondary indexes on said second member such that when said primary index is indexed with one of said at least two secondary indices said device is in said one position and when said primary index is indexed to another of said at least two secondary indexes, said device is in said second position.

7. The device as defined in claim 1 further comprising a primary index on said second member and at least two secondary indexes on said first member such that when said primary index is indexed with one of said two secondary indexes said device is in said one position and when said primary index is indexed to another of said at least two secondary indexes, said device is in said second position.

8. The device as defined in claim 1 further comprising a stop means for limiting the movability of said second member.

9. The device as defined in claim 8 wherein said stop means comprises a channel on said second member and a mating protrusion on said first member such that when said second member is moved it can move a distance equal in length as a length of said channel.

10. The device as defined in claim 9 wherein said channel has a first end and a second end such that when said second member is moved to said first end said device is in said one position and when said second member is moved to said second end said device is in said second position.

11. The device as defined in claim 1 further comprising a means to fill said dispensing chamber.

12. The device as defined in claim 11 wherein said means to fill comprises a fill tube on said second member adjacent to said dispensing chamber.

13. The device as defined in claim 11 wherein said means to fill comprises a removable cap.

14. The device as defined in claim 1 further comprising a means to discern the volume of the liquid substance within said dispensing chamber.

15. The device as defined in claim 14 wherein said means to discern comprises a view member on said second member adjacent to said dispensing chamber.

16. The device as defined in claim 1 further comprising means for sealing said opening of said first member from discharge communication with said outlet and for sealing said capillaries of said first member from discharge communication with said outlet.

17. The device as defined in claim 1 further comprising an outlet cap connectable to and removable from said outlet.

* * * * *